US005399778A

United States Patent [19]

Steffen et al.

[11] Patent Number: 5,399,778

[45] Date of Patent: Mar. 21, 1995

[54] PROCESS FOR THE PREPARATION OF KETALS

[75] Inventors: Klaus-Dieter Steffen, Hennef; Josef Metz, Marl, both of Germany

[73] Assignee: Hüls Aktiengesellschaft, Marl, Germany

[21] Appl. No.: 138,750

[22] Filed: Oct. 19, 1993

[30] Foreign Application Priority Data

Oct. 28, 1992 [DE] Germany ........................ 42 36 321.7
Aug. 28, 1993 [DE] Germany ........................ 43 29 033.7

[51] Int. Cl.[6] ............................................ C07C 41/56

[52] U.S. Cl. .................................... 568/591; 568/592; 568/594; 568/605

[58] Field of Search ................ 568/592, 594, 605, 591

[56] References Cited

U.S. PATENT DOCUMENTS 3,072,727 1/1963 Howard et al. ...................... 568/594
3,127,450 3/1964 Lorette et al. ...................... 568/594

OTHER PUBLICATIONS

Streitweiser et al, *Introduction to Organic Chemistry*, pp. 372–377, 1976.
Mackenzie et al, J. Organic Chemistry, (20), pp. 1695–1701, 1955.
Carswell et al., J. American Chemical Society, (50) pp. 235–241, 1928.

*Primary Examiner*—Johann Richter
*Assistant Examiner*—Michael B. Hydorn
*Attorney, Agent, or Firm*—Felfe & Lynch

[57] ABSTRACT

Ketals of longer-chain or branched alcohols are prepared from dimethyl ketals or their ketones by reaction of the dimethyl ketals and the alcohols at high temperatures of 150° to 180° C. in the presence of acid catalysts. The enol ethers and mixed ketals which are separated by distillation are added to the next reaction batch and also react to form the target product. The starting material, dimethyl ketal, may also be formed during the reaction from the ketone and trimethyl orthoformate.

8 Claims, No Drawings

PROCESS FOR THE PREPARATION OF KETALS

FIELD OF THE INVENTION

This invention relates to a novel process for the preparation of ketals by acid-catalyzed transketalization of dimethyl ketals containing at least one relatively long-chain alkyl group and/or an aryl radical, particularly ketals of cyclohexanone, with relatively long-chain or secondary alcohols.

BACKGROUND OF THE INVENTION

The preparation of ketals can be performed without difficulty only by starting from simple ketones, particularly from acetone, and short-chain alcohols by synthesis from the components or by transketalization. However, varying amounts of enol alkyl ethers are always formed, depending upon the structure of the reactants and the reaction conditions. In order to increase the degree of conversion, acid catalysts, molecular sieves or ion exchangers are employed, despite the fact that these compounds are difficult to handle.

Better conversions and higher yields of ketals are achieved by reacting ketones with orthoformic esters, but among the latter only the methyl and ethyl orthoesters can be satisfactorily prepared. Ketals having the complex structure of the formula II below can also be prepared by transketalization from dimethyl ketals, for instance as disclosed in U.S. Pat. No. 3,072,727, which are prepared from 2,2-dimethoxypropane (DMP from acetone). Ketals of the formula II, for example cyclohexanone diisopropyl ketal, are obtained with yields of only 30% (U.S. Pat. No. 3,072,727, Example VI) besides large amounts of various asymmetric ketals. The synthesis with 2,2-dimethoxypropane requires the use of entrainment agents, such as hexane or benzene, but these agents form an azeotrope with 2,2-dimethoxypropane. In claim 1 of U.S. Pat. No. 3,072,727 it is expressly stated that the reaction temperature must not exceed 100° C., because otherwise large amounts of various cyclohexene alkyl ethers are formed.

DESCRIPTION OF THE INVENTION

Therefore, the present invention relates to a novel process for the preparation of ketals by transketalization of a dimethyl ketal with an alcohol of the formula $R^2OH$ in the presence of an acid catalyst and accompanied by continuous removal of the methanol released by the reaction from the reaction mixture by distillation, characterized in that the dimethyl ketal is reacted with the alcohol $R^2OH$ to more than 90% completion at a temperature of 105° to 180° C. pursuant to the following reaction sequence:

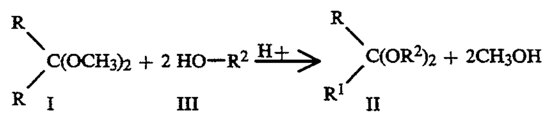

wherein

- R and $R^1$ are each independently alkyl of 1 to 8 carbon atoms or aryl, or
- R and $R^1$ together with each other are $—(CH_2)_4—$ or $—(CH_2)_5—$, and
- $R^2$ is linear or branched alkyl of 2 to 8 carbon atoms, the ketal of the alcohol $R^2OH$ is isolated by distillation, and the enol alkyl ether is recycled into the reaction. The substituent $R^2$ of the alcohol of the formula $R^2OH$ is preferably alkyl of 3 to 8 carbon atoms, most preferably branched alkyl of 3 to 8 carbon atoms.

The starting compound is the dimethyl ketal of the corresponding ketone, which is either pre-formed or prepared in advance from the ketone and trimethyl orthoformate (TMOF). This known reaction proceeds exothermically at 20° to 80° C. with virtually quantitative yields in the presence of an acid catalyst.

The process of the present invention is particularly well suited for the preparation of ketals of the formula II in which the ketal of formula I or the radical $R^2$ contains at least one alkyl group of 3 to 8 carbon atoms or a monocyclic aryl radical or a cycloalkyl radical, and/or in which the alkyl radical of the alcohol reactant is a relatively long-chain linear alkyl radical of 2 to 8 carbon atoms, especially branched alkyl of 2 to 8 carbon atoms. However, the process is especially well suited for the preparation of cyclohexyl or cyclopentyl ketals of branched chain alcohols, in particular of isopropanol or isobutanol. The process of the present invention is intentionally performed at high temperatures of 105° to 180° C., preferably 110° to 180° C., and especially preferably at 120° to 180° C. The reaction of all of the methoxy groups and their removal in the form of methanol by distillation results in a 90% or greater conversion of the alcohol of the formula III with the ketal of the formula I into the ketal of formula II. Final temperatures of 150° to 180° C. in the preparation of the target products of the formula II are of particular advantage.

The formation of enol alkyl ethers, that is, ethers of unsaturated alcohols which correspond to the alkanol of the formula $R^2OH$ is intentionally accepted because we have found that the target product of the formula II has the highest boiling point of all of the reactants, on average 20° above the other ketals and the ethers. The enol ether is formed in amounts of 0 to 30 mol-%, but this does not represent a loss because the enol ether can be removed by distillation, like the mixed ketals, optionally as a joint fraction, and added to a subsequent batch or to the same batch in unpurified form. Before this distillation, all of the low-boiling reaction mixture components, namely methanol and the excess of alcohol, as well as esters and ethers, are separated.

The high temperature permits the reaction to be performed within a short period of time. Moreover, the process of the present invention has the considerable advantage that the use of entrainment agents is not required in contradistinction to the prior art processes.

The catalysts to be used in the reaction according to the present invention are acid compounds, even though it is known that acetals and ketals release alcohol under acid conditions. Examples of suitable acid catalysts are p-toluenesulfonic acid, sulfuric acid, acid ion exchangers, boron trifluoride complexes, ammonium chloride, inter alia, in amounts of 0.1 to 0.4 g of acid per mol of ketone.

The acid catalyst is advantageously already present in the reaction mixture if the dimethyl ketal is prepared in advance from trimethyl orthoformate.

The acid catalyst should be neutralized before the distillation by addition of alkalis, advantageously by the addition of alkali metal alkoxides, especially sodium alkoxides, and particularly an alkali metal alkoxide of the alcohol of the formula III, in at least an equivalent amount.

A further subject of the present invention is a process for the preparation of ketals of the formula II in which, simultaneously with the preparation of these ketals from dimethyl ketals and an alcohol of the formula III, the dimethyl ketal of the formula I is formed from the corresponding ketone and trimethyl orthoformate.

Advantageously, the acid catalysts referred to above are already present in the reaction mixture from the start. In this method of operation some of the alcohol of the formula III may be provided at the beginning and the remainder can be added at a later time. Preferably, the ketone, for instance cyclohexanone, and isopropanol are first introduced into the reaction vessel, trimethyl formate is added at as high a sump temperature as possible, and methyl formate and methanol are distilled off.

Suitable temperatures at the beginning of the reaction are between 75° and 120° C. By means of the addition of isopropanol, mixed ketals are converted into diisopropyl ketal.

Yields of 90 to 96% pure ketal, based on the amount of ketone, are achievable.

Finally, the process of the instant invention almost completely avoids the formation of mixed ketals and enol ethers which are formed in such large amounts in the processes of the prior art.

The following examples illustrate the present invention and will enable others skilled in the art to understand it more completely. It should be understood, however, that the invention is not limited solely to the particular examples given below.

EXAMPLE 1

Preparation of Cyclohexanone Diisopropyl Ketal (CHIPK)

196.3 g of cyclohexanone (2.0 mols), 10.9 g of methanol (0.34 mol) and 0.4 g of p-toluenesulfonic acid were introduced into a 1-liter 4-necked flask equipped with a stirrer, a thermometer and a fractional distillation column. While cooling the flask on a water bath, 212.5 g of trimethyl orthoformate (2.0 mols) were added dropwise over the course of 1 hour at a temperature of 18° to 25° C., and the reaction was allowed to go to completion for 1.5 hours.

According to gas-chromatographic analysis, the composition of the reaction mixture was as follows:

85% cyclohexanone dimethyl ketal (CHMK)
2% methanol
12% methyl formate
and traces of cyclohexanone.

481 g of isopropanol (8 mols) were added to this mixture of products in the same flask, and the resulting mixture was heated whereby under reflux all of the low-boiling-point components, i.e. methyl formate, methanol, isopropyl formate and isopropanol, distilled off over the course of 2 hours during which the reaction temperature was gradually increased to 125° to 130° C. Another 0.4 g of p-toluenesulfonic acid was added after half the distillation time.

After 15 hours the reaction was 95% complete, and the average composition of the reaction mixture was as follows:

45% CHIPK
40% isopropanol
6% cyclohexene isopropyl ether
5% cyclohexanone methyl isopropyl mixed ketal.

1 g of sodium isopropoxide was added to the mixture to neutralize the p-toluenesulfonic acid, and under a partial vacuum of 500 to 250 hPa, pure isopropanol was removed by distillation and recycled into subsequent batches. After increasing the vacuum to 20 hPa, a second fraction containing the cyclohexene isopropyl ether, the mixed ketals, small amounts of isopropanol and cyclohexanone, and some CHIPK were removed by distillation under reflux. The cyclohexanone diisopropyl ketal target product was then removed by distillation at a head temperature of 89° to 90° C./20 hPa (65° C./5 hPa ).

Yield: 250 g (62.4% of theory, based on the amount of cyclohexanone starting compound) gas-chromatographic purity: 98.3% CHIPK.

EXAMPLES 2 TO 5

Preparation of Cyclohexanone Diisopropyl Ketal (CHIPK)

The starting compound, cyclohexanone dimethyl ketal was prepared as described in Example 1. The ketal target product was prepared as described in Example 1, but the second fraction from preceding batches with specific contents of cyclohexene isopropyl ether on average was added, and corresponding fresh cyclohexanone or its dimethyl ketal was added to make up to 2.0 mols. The isopropanol consisted in part of recycled isopropanol. The performance of the transketalization as well as of the initial and purification distillations were carried out as described in Example 1. The yields and other data relative to Examples 2 to 5 are shown in the following Table.

| Reaction parameters | Examples 2 | 3 | 4 | 5 |
|---|---|---|---|---|
| Starting materials: | | | | |
| Crude CHMK* (g/mol) | 285/1.34 | 292/1.39 | 274/1.31 | 279/1.33 |
| Isopropanol | | | | |
| fresh (g/mol) | 333/5.55 | 278/4.63 | 253/4.22 | 237/3.94 |
| recycled (g/mol) | 148/2.45 | 203/3.37 | 227/3.78 | 244/4.06 |
| Preliminary fractions from the preceding batch | 1 | 2 | 3 | 4 |
| (g/mol) | 113/0.66 | 96/0.61 | 104/0.69 | 114/0.67 |
| p-toluenesulphonic acid (g) | 0.4 | 0.4 | 0.4 | 0.4 |
| Sodium isopropoxide (g) | 1 | 1 | 1 | 1 |
| CHIPK pure distillate: | | | | |
| Amount (g) | 258 | 248 | 237 | 245 |
| Purity (GC %) | 98.0 | 98.3 | 98.8 | 98.3 |
| Yield (% of theory) (based on CHMK) | 96.1 | 89.0 | 90.3 | 91.9 |

*CHMK = cyclohexanone dimethyl ketal

EXAMPLE 6

Preparation of Cyclohexanone Diisobutyl Ketal (CHIBK)

Cyclohexanone dimethyl ketal (CHMK) was prepared as described in Example 1 from 1 mol of cyclohexanone and trimethyl orthoformate. 370.6 g of isobutanol (2-methyl-1-propanol, 5.0 mols) were added, and the transketalization was then carried out under reflux while the sump temperature was gradually increased from 110° to 160° C. After a running time of 2 hours, another 0.4 g of p-toluenesulfonic acid was added. The low-boiling-point components, i.e. methyl formate, methanol and a small amount of isobutyl formate, were removed by distillation under reflux (ratio 1:5 to 1:2) over the course of 4 hours.

Since the sump analysis exhibited values of 79% CHIBK, 16% isobutanol, and 1% each of methyl isobutyl mixed ketal, cyclohexanone and cyclohexene ether (more than 90% conversion of cyclohexanone), the reaction mixture was neutralized with 1 g of sodium methylate, and the distillation was commenced. Under reduced pressure of initially 20 hPa and then further reduced to 5 hPa, isobutanol and the other side products were distilled off. At a boiling point of 98° C./5 hPa without reflux the cyclohexanone diisobutyl ketal was removed at the head of the column. The preliminary fraction which distilled off in advance was composed of 95 g (65% isobutanol, 17% CHIBK, cyclohexanone, cyclohexene ether and mixed ketals), together 0.21 mol CHIBK, cyclohexanone and derivatives thereof.

The preliminary fraction was recycled into Example 7.

Yield: 352 g (75.5% of theory, based on cyclohexanone) Purity: 98.0% (gas-chromatography).

EXAMPLE 7

Preparation of Cyclohexanone Diisobutyl Ketal (CHIBK)

A 2-mol-batch of cyclohexanone dimethyl ketal was prepared as described in Example 6, and after addition of 370.6 g of isobutanol (5.0 mols) as well as 95 g of the preliminary fraction from Example 6, it was transketalized at an increasing sump temperature of 105° C. to 160° C. All of the methanol, the formate and some isobutanol distilled off at a reflux ratio of 1:2 over the course of 4 hours. Thereafter the reaction solution was composed of 23% isobutanol, 68% CHIBK, 2% each of cyclohexanone and mixed ketal as well as a small amount of cyclohexene ether. The acid catalyst was then neutralized with 0.5 g of sodium methylate, and the mixture was distilled under a gradual increase in vacuum of 20 hPa to 5 hPa. 177 g of a preliminary fraction distilled over which contained 75% isobutanol, 10% CHIBK and the remainder cyclohexanone, cyclohexene ether and mixed ketal, with 0.251 mol of potential CHIBK (12.6% yield). The target product distilled over at 97° to 98° C./5 hPa. CHIBK purity: 98.4% (gas-chromatography)

Yield: 394 g=84.9% of theory, based on 2.0 mols of cyclohexanone; 88.2% of theory, including the preliminary fractions.

EXAMPLE 8

Preparation of Cyclohexanone Diisopropyl Ketal

Amounts of reactants:

327.2 g (3.33 mols) cyclohexanone
0.67 g (0.004 mol) p-toluenesulfonic acid
400.0 g (6.66 mols) isopropanol (first amount)
392.5 g (6.53 mols) isopropanol (second amount)
353.7 g (3.33 mols) trimethyl orthoformate Apparatus:

Heated 2-liter flask with stirrer, dropping funnel, 1-meter column with packings, vapor separator, reflux cooler and distillate providing system under protective nitrogen atmosphere.

Performance:

Cyclohexanone, the first amount of isopropanol and p-toluenesulfonic acid were introduced into the flask. The temperature was adjusted to 80° C., and trimethyl orthoformate was added dropwise over a period of 3 hours. The methyl formate/methanol mixture was removed at the head of the column (column temperature at the head 40° to 60° C.).

Thereafter the sump temperature was increased stepwise to 115° C., and further methanol was removed at the head under strong reflux. After a running time of 10 hours the second amount of isopropanol was metered in. After a running time of 30 hours the content of CHIPK (in FID-surface-%) was 56.7.

Work-Up:

The reaction mixture was admixed with sodium methylate in methanolic solution. At 300 hPa and 40° C. head temperature a fraction of isopropanol and low boiling point side products was separated under a reflux ratio of 1:1, and the fraction was added to a subsequent batch. Thereafter the reaction mixture was distilled to purity at 5 hPa and 85° C. The product contained more than 97.5% CHIPK (FID-surface-%).

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. In the method of preparing a ketal by transketalizing a dimethyl ketal with an alcohol of the formula $R^2OH$ in the presence of an acid catalyst and distilling off the methanol released by the reaction, the improvement which comprises reacting said dimethyl ketal with said alcohol of the formula $R^2OH$ to more than 90% completion by bringing the reaction temperature to 150° to 180° C. pursuant to the reaction sequence

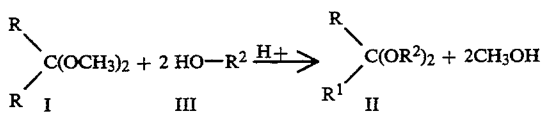

wherein

R and $R^1$ are each independently alkyl of 1 to 8 carbon atoms or aryl, or

R and $R^1$ together with each other are $-(CH_2)_4-$ or $-(CH_2)_5-$, and $R^2$ is linear or branched alkyl of 2 to 8 carbon atoms, and separating the ketal of the formula II by distillation without a solvent.

2. The method of claim 1, wherein the acid catalyst is neutralized prior to separating the ketal by distillation.

3. The method of claim 1, wherein the ketal of the formula II is the ketal of cyclohexanone or cyclopentanone.

4. The method of claim 1, wherein the dimethyl ketal of the formula I is formed by reaction of trimethyl orthoformate with a corresponding ketone in the presence of an acid catalyst, and the reaction mixture is reacted into the ketal of the formula II without work-up.

5. The method of claim 1, wherein, simultaneously with the preparation of the ketal of the formula II from dimethyl ketal of the formula I, the dimethyl ketal of the formula I is formed from the corresponding ketone and trimethyl orthoformate.

6. The method of claim 5, wherein the reaction is carried out in the presence of an acid catalyst.

7. The method of claim 5, wherein the reaction temperature at the beginning of the reaction is between 75° and 120° C.

8. The method of claim 1, wherein the side products formed during the preparation of the ketal of the formula II are recycled into the reaction mixture.

* * * * *